(12) United States Patent
Evers et al.

(10) Patent No.: US 7,998,751 B2
(45) Date of Patent: Aug. 16, 2011

(54) METHOD AND APPARATUS FOR ASPIRATING AND DISPENSING SMALL LIQUID SAMPLES IN AN AUTOMATED CLINICAL ANALYZER

(75) Inventors: Timothy Patrick Evers, Wilmington, DE (US); Antoine Elias Haddad, Newark, DE (US)

(73) Assignee: Siemens Healthcare Diagnostics Inc., Deerfield, IL (US)

(*) Notice: Subject to any disclaimer, the term of this patent is extended or adjusted under 35 U.S.C. 154(b) by 1291 days.

(21) Appl. No.: 11/114,351

(22) Filed: Apr. 26, 2005

(65) Prior Publication Data

US 2006/0239860 A1    Oct. 26, 2006

(51) Int. Cl.
*G01N 1/10* (2006.01)
(52) U.S. Cl. ........................ 436/180; 422/500
(58) Field of Classification Search .................. 436/180; 422/100, 500
See application file for complete search history.

(56) References Cited

U.S. PATENT DOCUMENTS

| | | | |
|---|---|---|---|
| 3,752,197 A * | 8/1973 | Ambrose et al. .................. 141/1 |
| 4,108,608 A * | 8/1978 | Maher et al. ............... 73/864.12 |
| 4,504,444 A * | 3/1985 | Englander ..................... 422/100 |
| 4,821,586 A * | 4/1989 | Scordato et al. ........... 73/864.18 |
| 4,871,682 A | 10/1989 | Mazza ......................... 436/179 |
| 5,037,623 A * | 8/1991 | Schneider et al. ............ 422/292 |
| 5,216,926 A | 6/1993 | Lipscomb .................. 73/864.25 |
| 5,452,619 A * | 9/1995 | Kawanabe et al. ........ 73/864.01 |
| 5,488,874 A | 2/1996 | Kanwanabe et al. ...... 73/863.01 |
| 5,558,838 A | 9/1996 | Uffenheimer ................ 422/100 |
| 5,743,960 A | 4/1998 | Tisone ......................... 118/683 |
| 5,763,278 A | 6/1998 | Sickinger et al. ............. 436/180 |
| 5,814,277 A | 9/1998 | Bell et al. ........................ 422/67 |
| 5,846,491 A * | 12/1998 | Choperena et al. ............. 422/67 |
| 5,916,524 A | 6/1999 | Tisone ......................... 422/100 |
| 5,918,291 A | 6/1999 | Inacu et al. ................ 73/863.83 |
| 5,927,547 A | 7/1999 | Papen et al. ..................... 222/57 |
| 6,143,573 A * | 11/2000 | Rao et al. ..................... 436/180 |
| 6,146,592 A * | 11/2000 | Kawashima et al. ........... 422/67 |
| 6,203,759 B1 | 3/2001 | Pelc et al. ..................... 422/100 |
| 6,422,431 B2 | 7/2002 | Pelc et al. ..................... 222/422 |
| 6,562,232 B2 * | 5/2003 | Myogadani .................... 210/94 |
| 6,589,791 B1 | 7/2003 | La Budde et al. .............. 436/55 |
| 6,709,872 B1 * | 3/2004 | Downs et al. ................. 436/180 |
| 6,962,782 B1 * | 11/2005 | Livache et al. .................... 435/6 |
| 7,097,808 B1 * | 8/2006 | Onuma ........................... 422/63 |
| 7,220,385 B2 * | 5/2007 | Blecka et al. .................... 422/64 |
| 2001/0055545 A1 * | 12/2001 | Takii et al. .................... 422/100 |
| 2002/0114740 A1 * | 8/2002 | Yamamoto .................... 422/100 |
| 2006/0216207 A1 * | 9/2006 | Lehto ............................ 422/100 |

* cited by examiner

*Primary Examiner* — Brian R Gordon
(74) *Attorney, Agent, or Firm* — Leland K. Jordan

(57) ABSTRACT

Providing the desired volume of a liquid within a biochemical analyzer by aspirating an excess slug of liquid from a container into a probe, ejecting a portion of the excess liquid, and then dispensing the desired volume of liquid into a container.

6 Claims, 11 Drawing Sheets

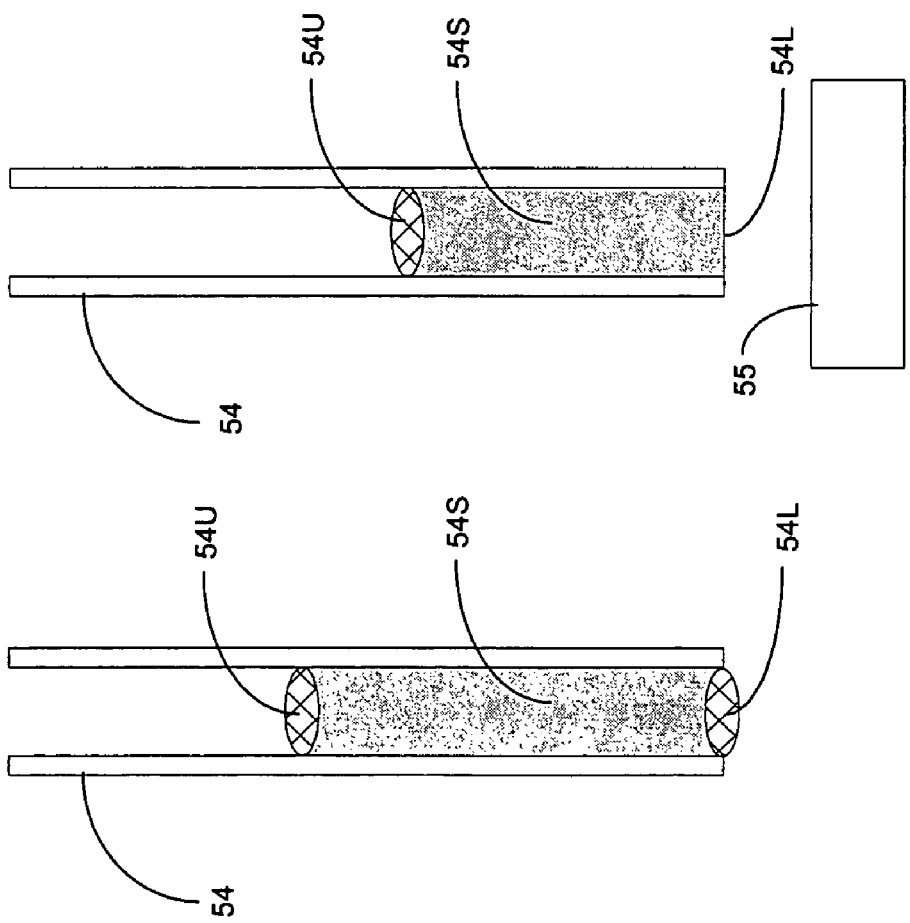

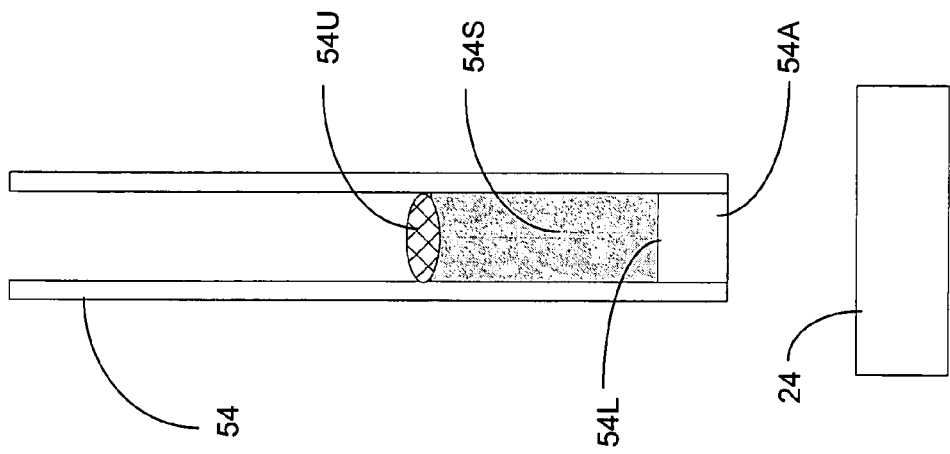
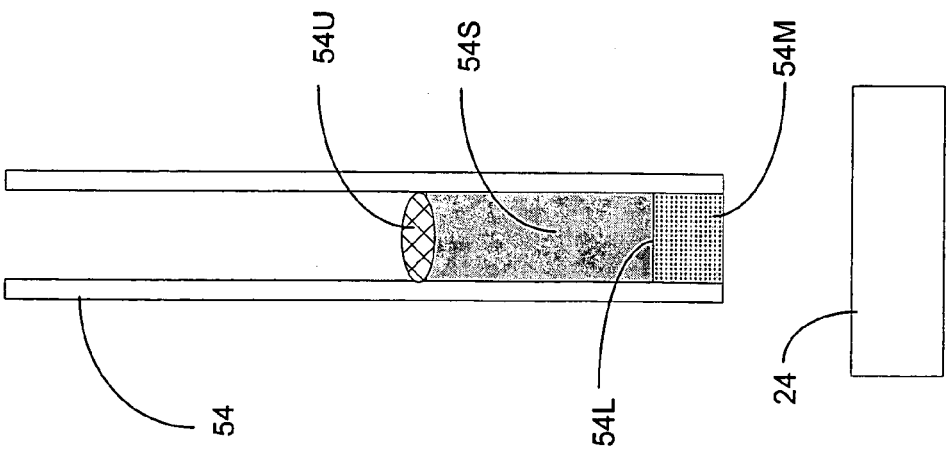

METHOD AND APPARATUS FOR ASPIRATING AND DISPENSING SMALL LIQUID SAMPLES IN AN AUTOMATED CLINICAL ANALYZER

FIELD OF THE INVENTION

The present invention relates to a method and apparatus for accurately dispensing small liquid samples, reagents, or other solutions into a container. In particular, the present invention provides a method for minimizing uncontrolled liquid volume variations during aspiration and dispensing processes that can occur as a result of operating within the vagaries of an electromechanical environment like found within an automated clinical analyzer.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts liquid sample from the vial and combines the sample with various reagents in special reaction cuvettes or tubes. Usually the sample-reagent solution is incubated or otherwise processed before being analyzed. Analytical measurements are often performed using a beam of interrogating radiation interacting with the sample-reagent combination, for example turbidimetric, fluorometric, absorption readings or the like. The measurements allow determination of end-point or rate values from which an amount of analyte related to the health of the patient may be determined using well-known calibration techniques.

A clinical analyzers employs many different processes to identify analytes and throughout these processes, patient liquid samples, and samples in combination with various other liquids like reagents or diluents or re-hydrated compositions, are frequently required to be mixed to a high degree of uniformity. Due to increasing pressures on clinical laboratories to increase analytical sensitivity, there continues to be a need for improvements in the overall processing accuracy of clinical analyzers, even with a trend to employ smaller and smaller patient samples. In particular, liquid sample handling needs to be more accurate in terms of providing a small but well known volume of liquid sample for analysis, producing a need for a sampling technique having a high degree of uniformity, without unduly increasing analyzer cost or requiring a disproportional amount of space. The sampling system vagaries that arise from uncontrolled variations in pumping tube lengths, pumping piston displacements, vacuum levels within closed sample tubes, electromechanical vibrations, and the like, can cause analysis inaccuracies in particular in the instance that small samples, in the range of one microliter, are being aspirated and subsequently analyzed.

Various methods have historically been implemented to provide uniform and known small sample liquids. U.S. Pat. No. 6,589,791 discloses a state-variable feedback control system for controlling the operation of a microfluidic aspirate dispense-system using measurements from one or more pressure sensors to derive information for active feedback control in order to dispense liquid drops of different sizes.

U.S. Pat. No. 6,203,759 discloses a microvolume liquid handling system, a system reservoir is connected with tubing to a pressure control system for controlling the liquid system pressure in the system reservoir. The system reservoir is coupled to one or more microdispensers through a distribution tube having a branched section for each microdispenser. In this embodiment, each microdispenser is coupled to its own flow sensor and to enable a system controller to respectively measure and control the flow of liquid in the each microdispenser.

U.S. Pat. No. 5,927,547 discloses a low volume liquid handling system with a microdispenser employing a piezoelectric transducer attached to a glass capillary, a positive displacement pump for priming and aspirating liquid into the microdispenser, controlling the pressure of the liquid system, and washing the microdispenser between liquid transfers. A pressure sensor is used to measure the liquid system pressure and produce a corresponding electrical signal.

U.S. Pat. No. 5,916,524 discloses an apparatus for dispensing precise quantities of reagents is disclosed including a positive displacement syringe pump in series with a dispenser, such as an aerosol dispenser or solenoid valve dispenser. The pump is controlled by a stepper motor or the like to provide an incremental quantity or continuous flow of reagent to the dispenser.

U.S. Pat. No. 5,763,278 discloses a device for automated pipetting of small volumes of liquid has a pipetting needle, a diluter having a liquid output with a syringe and a valve, the syringe including a piston and a piston drive.

U.S. Pat. No. 5,743,960 discloses a reagent dispensing apparatus is provided including a positive displacement syringe pump in series with a solenoid valve dispenser.

U.S. Pat. No. 5,558,838 discloses a sample preparation apparatus that uses a pair of valves including a first shear valve and a second vent/aspiration valve to control liquid flow between a sample tube, a reaction tube, the atmosphere, a waste pump, and a diluent pump.

U.S. Pat. No. 5,216,926 discloses an automatic sampling apparatus using fluid driven actuators whose control system provides accurate positioning over its range of motion. The actuators are positioned to aspirate liquid contents held within stoppered sample containers and equilibrate pressure in the sample containers to atmospheric prior to aspiration.

Accordingly, from a study of the different approaches taken in the prior art to the problems encountered with aspirating and dispensing precise and known small amounts of liquid solutions, there is a need for an improved approach to the design of a simplified, space-efficient liquid sample and or sample-reagent mixer. In particular, there is a continuing need for a method for eliminating the unknown variabilities that can exist at the upper and lower end portions of an aspirated liquid slug inside a sampling probe.

SUMMARY OF THE INVENTION

The principal object of the invention is to provide an improved method for providing known and controlled small amounts of liquids at a precisely desired volume within a biochemical analyzer by eliminating the unknown variabilities that can exist at the upper and lower end portions of an aspirated liquid slug inside a sampling probe. The liquid slug is purposefully overdrawn so that an excess of liquid over the desired liquid volume is aspirated into the probe. Because the bottom end portion of the liquid slug could form a droplet at the open end of the probe, or even form a cusp into the interior of the probe, a small portion of the overdrawn liquid is ejected into a drain in order to produce a known liquid state bottom end portion of the liquid slug at the open end of the probe. Next, the pumping system is precisely operated to dispense a known and precisely controlled amount of desired liquid that is less than the volume of remaining overdrawn liquid slug in the probe. By purposefully retaining the uppermost portion of the overdrawn liquid slug in the probe, the potential inaccuracies associated with not knowing the exact location of the upper end portion of the original overdrawn liquid slug are eliminated.

In the instance that the aspirated liquid is patient sample to be analyzed and the aspirated sample is dispensed into a reaction cuvette already containing another liquid like one or more reagents, the pumping system is operated to dispense the precisely controlled amount of liquid from the probe when positioned near the bottom of the liquid receiving cuvette. The probe is then raised towards the top of the liquid mixture therein. While the sampling probe is still within the liquid mixture, a small amount of mixture is aspirated into the probe so that the sample liquid is safely trapped within the probe. The probe may then safely be used as a mixing swizzle to mix the sample-reagent mixture without concern for additional sample to be dripped into the cuvette. By using aspiration probe as a mixing swizzle instead of the conventional practice of having a separate mixer, economy in production costs as well as space are achieved in addition to increasing overall system reliability by the elimination of a separate electromechanical device.

Alternately, the pumping system may be operated to dispense the liquid from the probe and to then raise the probe above the top of the reagent liquids. While the sampling probe is above the reagent mixture, a small amount of air may be aspirated into the probe so that the sample liquid is safely trapped within the probe. The probe can then safely be lowered into the sample-reagent mixture and used as a mixing swizzle to mix the sample-reagent mixture without concern for sample being dropped into the cuvette.

BRIEF DESCRIPTION OF THE DRAWINGS

The invention will be more fully understood from the following detailed description thereof taken in connection with the accompanying drawings which form a part of this application and in which:

FIGS. 6A-6C are schematic illustrations of the aspiration and dispensing processes in accord with the present invention;

FIGS. 6D-6E are schematic illustrations of an aspiration process useful before mixing in accord with the present invention;

DETAILED DESCRIPTION OF THE INVENTION

Figure 1:
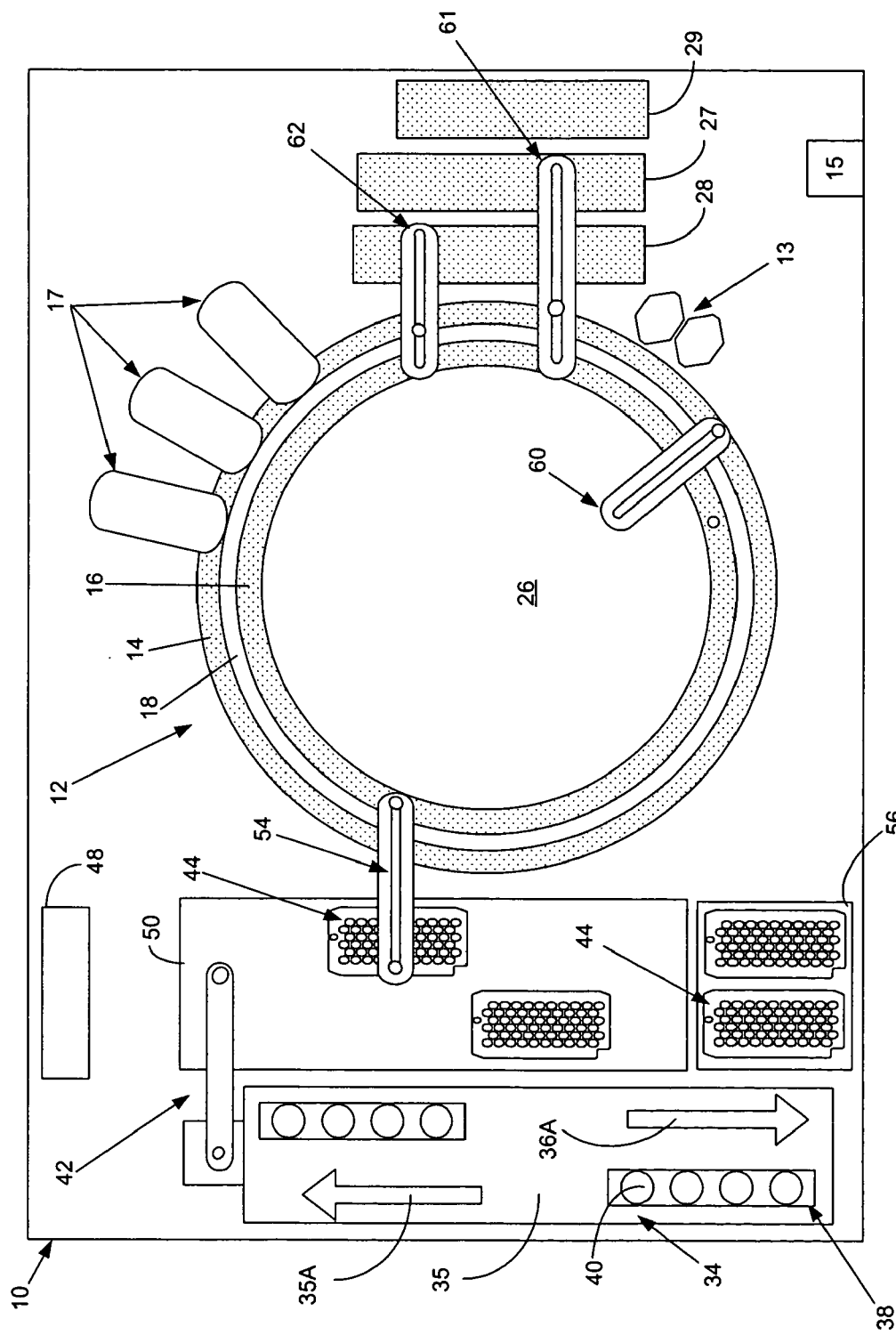
FIG. 1 is a schematic plan view of an automated analyzer adapted to perform the present invention.
Figure 2:
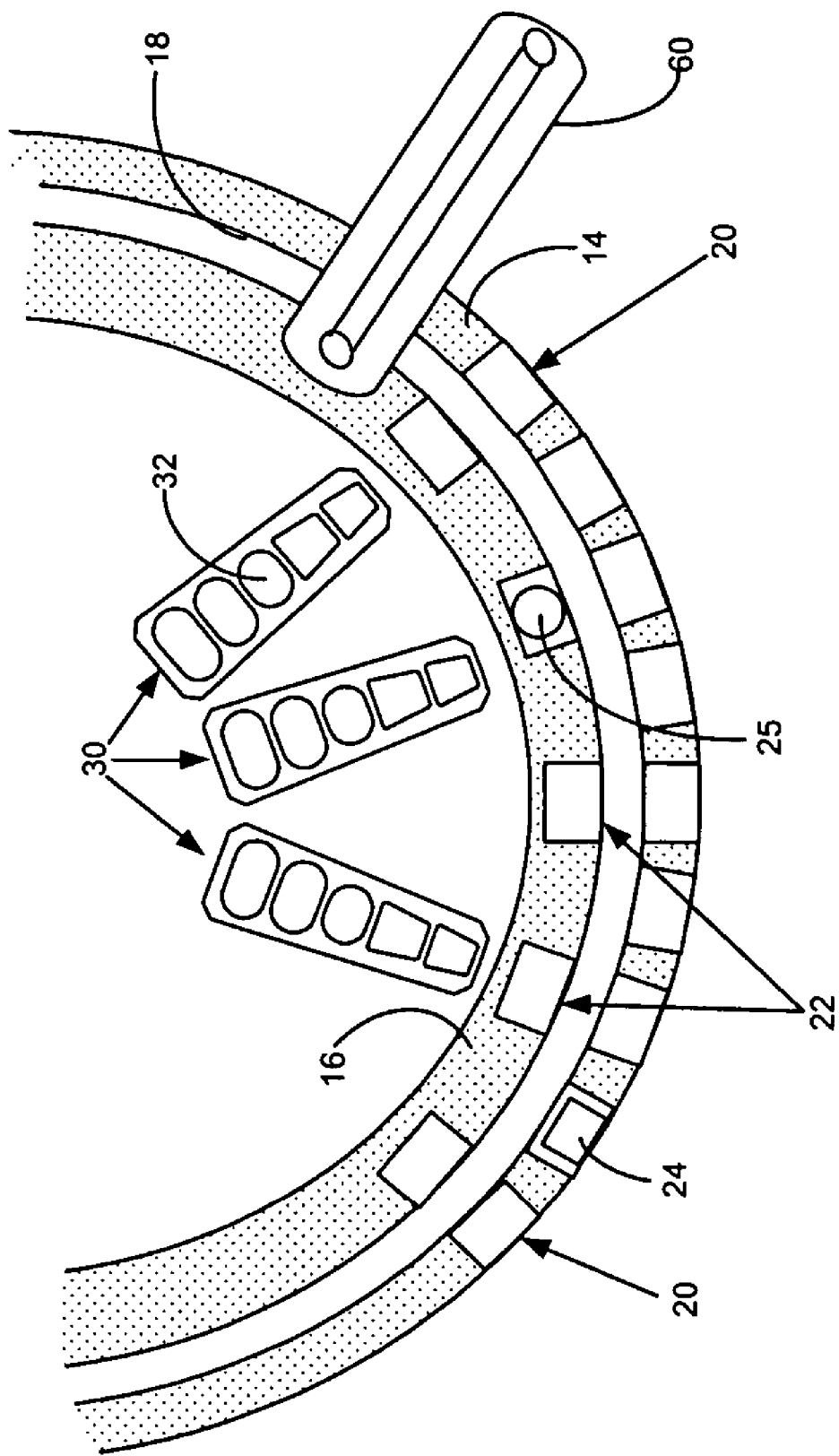
FIG. 2 is an enlarged schematic plan view of a portion of the analyzer of FIG. 1.
Figure 2A:
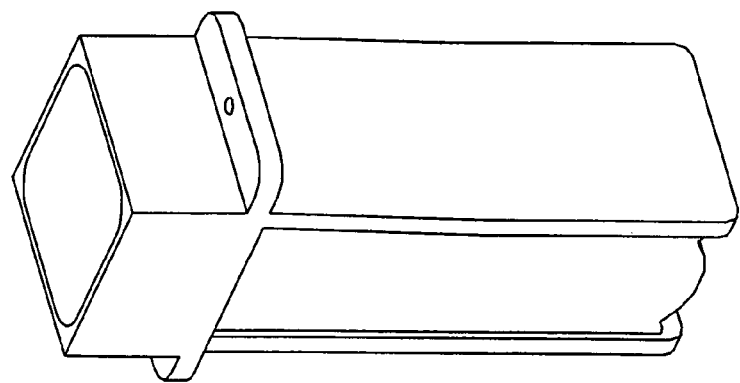
FIG. 2A is perspective view of a reaction cuvette useful in operating the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer carousel 14 having cuvette ports 20 formed therein and an inner carousel 16 having vessel ports 22 formed therein, the outer carousel 14 and inner carousel 16 being separated by a open groove 18. Cuvette ports 20 are adapted to receive a plurality of reaction cuvettes 24, like seen in FIG. 2A, that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which reaction carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

As seen in FIG. 1, a bi-directional incoming and outgoing sample fluid tube transport system 34 comprises a mechanism for transporting sample fluid tube racks 38 containing open or closed sample fluid containers such as sample fluid tubes 40 from a rack input load position at a first end of the input lane 35 to the second end of input lane 35 as indicated by open arrow 35A. Liquid specimens contained in sample tubes 40 are identified by reading bar coded indicia placed thereon using a conventional bar code reader to determine, among other items, a patient's identity, tests to be performed, if a sample aliquot is to be retained within analyzer 10 and if so, for what period of time. It is also common practice to place bar coded indicia on sample tube racks 38 and employ a large number of bar code readers installed throughout analyzer 10 to ascertain, control and track the location of sample tubes 40 and sample tube racks 38.

Figure 3:
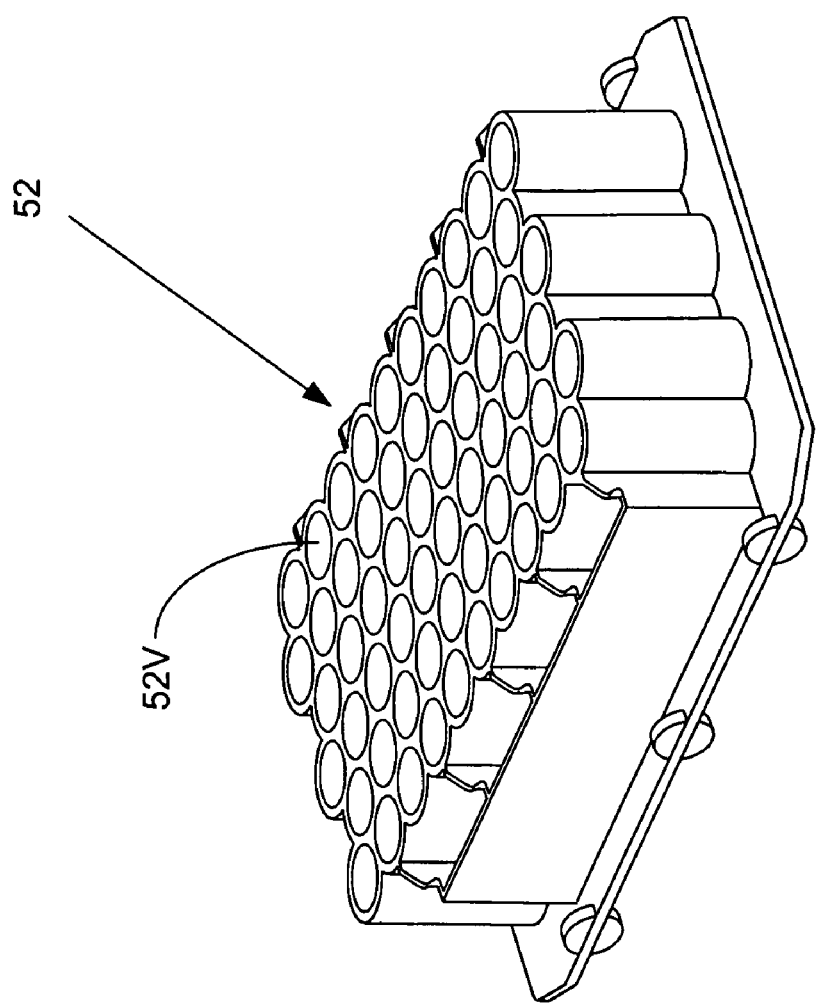
FIG. 3 is perspective view of an aliquot vessel array useful in the analyzer of FIG. 1.
Figure 4:
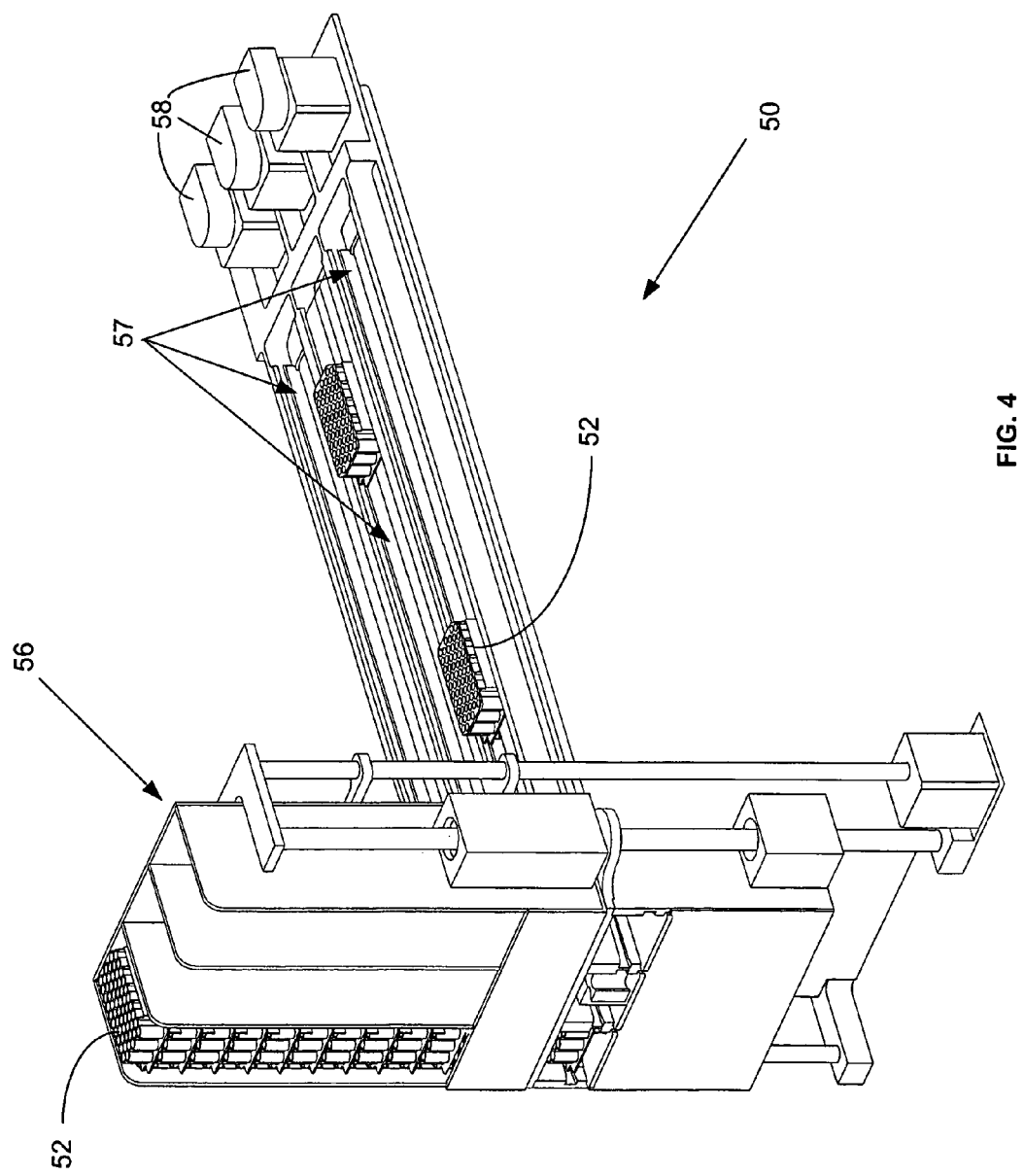
FIG. 4 is a perspective view of an aliquot vessel array storage and handling unit of the analyzer of FIG. 1.

A conventional liquid sampling probe 42 is located proximate the second end of the input lane 35 and is operable to aspirate aliquot portions of sample fluid from sample fluid tubes 40 and to dispense an aliquot portion of the sample fluid into one or more of a plurality of vessels 44V in aliquot vessel array 44, seen in FIG. 3, depending on the quantity of sample fluid required to perform the requisite assays and to provide for a sample fluid aliquot to be retained by analyzer 10 within an environmental chamber 48. After sample fluid is aspirated from all sample fluid tubes 40 on a rack 38 and dispensed into aliquot vessels 44V maintained in an aliquot vessel array storage and transport system 50 seen in FIG. 4, rack 38 may be moved, as indicated by open arrow 36A, to a front area of analyzer 10 accessible to an operator so that racks 38 may be unloaded from analyzer 10.

Aliquot vessel array transport system 50 seen in FIG. 5 comprises an aliquot vessel array storage and dispensing module 56 and a number of linear drive motors 58 adapted to bi-directionally translate aliquot vessel arrays 52 within a number of aliquot vessel array tracks 57 below a sample aspiration needle probe 54 and roller mixing assembly 56, described hereinafter, located proximate reaction carousel 12. Sample aspiration probe 54 is controlled by computer 15 and is adapted to aspirate a controlled amount of sample from individual vessels 52V positioned at a sampling location within a track 57 and is then shuttled to a dispensing location where an appropriate amount of aspirated sample is dispensed into one or more cuvettes 24 for testing by analyzer 10 for one or more analytes. In accord with the present invention, in order to eliminate the unknown variabilities that can exist at the upper end portion 54U and lower end portion 54L of an aspirated liquid slug 54S of sample inside aspiration probe 54 as illustrated by cross-hatched ovals in FIG. 6A, the liquid slug 54S is purposefully overdrawn so that an excess of sample over the desired sample volume is aspirated into probe 54. For example, in the event a volume in the range of 1 microliter of sample is desired, and extra 3-4 microliter of liquid is aspirated. Because the lower end portion 54L of the liquid slug 54S could form an unknown volume droplet at the open lower end of probe 54, or even form an unknown volume cusp into the interior of probe 54, a small portion of the overdrawn liquid slug 54S in the range of about 1 microliter is ejected into a drain 55 as seen in FIG. 6B in order to produce a known liquid state at the lower end portion 54L of the liquid slug 54S at the open end of probe 54. Probe lower end portion 54L may be cleaned using known techniques, for example with an air knife, to improve reproducibility.

Next, Pump Module 60P described hereinafter is precisely operated to dispense a known and controlled amount of desired sample that is less than the about 3-4 microliter volume of remaining overdrawn liquid slug 54S in probe 54 into a cuvette 24, as illustrated in FIG. 6C. By purposefully retaining the upper end portion 54U of the overdrawn liquid slug 54S in probe 54, the potential inaccuracies associated with not knowing the exact location and shape of the upper end portion 54U of the original overdrawn liquid slug 54S are eliminated. In order to avoid further variability associated with not knowing the exact location and shape of the upper end portion 54U, a portion of the first liquid may remain in the probe after dispensing. After sample has been dispensed into reaction cuvette 24, conventional transfer means move aliquot vessel arrays 52 as required between aliquot vessel array transport system 50, environmental chamber 48 and a disposal area, not shown.

Figure 7:
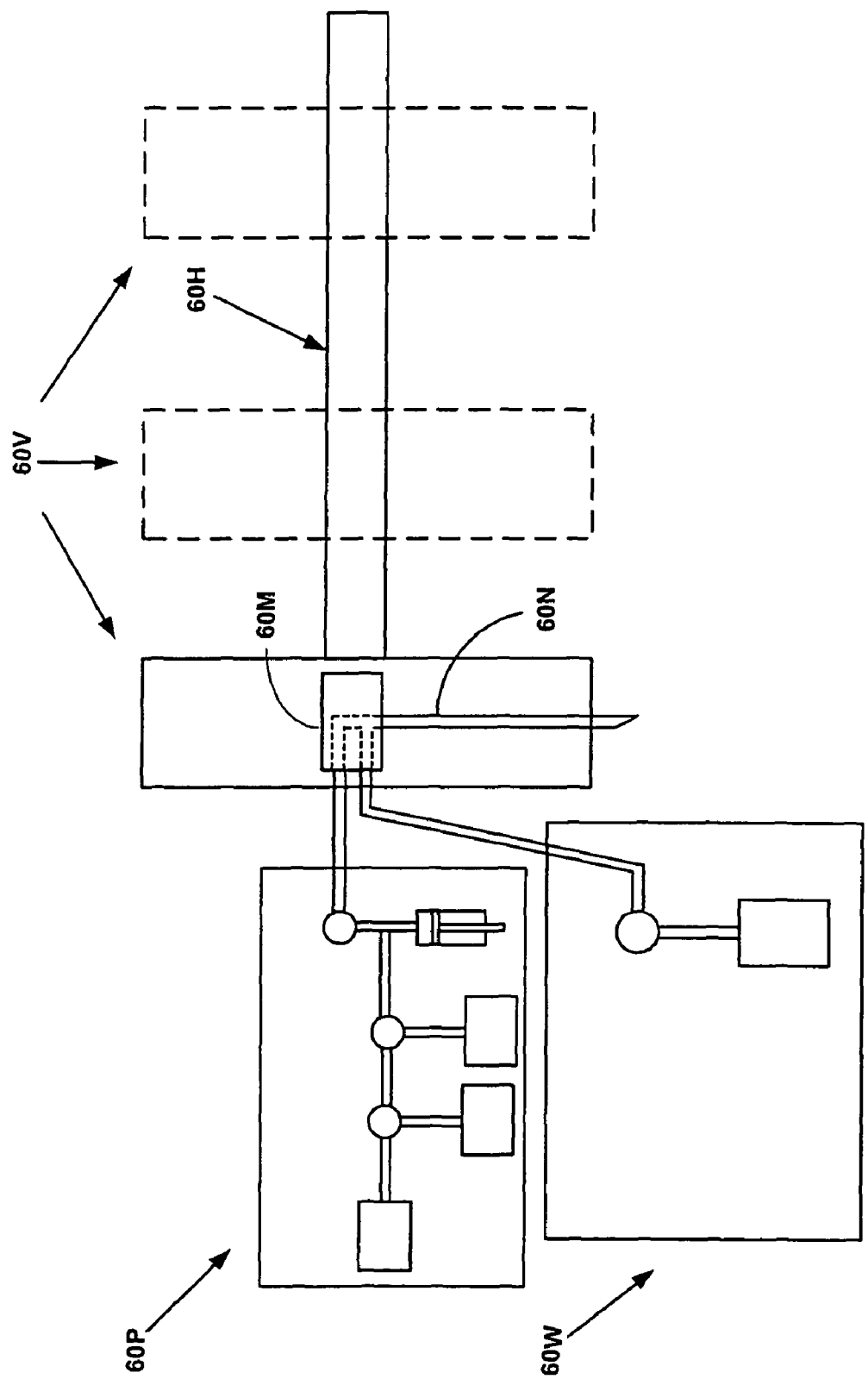
FIG. 7 is a schematic view of a liquid aspiration and dispensing system useful in performing the present invention.

Aspiration probe 54 useful in performing the present invention may be seen in FIG. 7 as associated with a Horizontal Drive component 60H, a Vertical Drive component 60V, a Wash Module component 60W, a Pump Module component 60P, an aspiration and dispensing needle 54, and a Wash Manifold component 60M having the primary functions described in Table 1. Components of Pump Module component 60P unidentified in FIG. 7 are described in FIG. 8. Horizontal Drive component 60H and Vertical Drive component 60V are typically computer controlled stepper motors or linear actuators and are controlled by computer 15 for providing precisely controlled movements of the Horizontal Drive component 60H and Vertical Drive component 60V.

TABLE 1

| Module | Primary Functions |
| --- | --- |
| Horizontal Drive 60H | Position the Vertical Drive 42V over reagent cartridges 30 containing reagent liquids and carried in a vial rack 30A and over cuvettes 24 carried in ports 20. |
| Vertical Drive 60V | Drive probe 60P through the covering of a reagent cartridge 30. |
| Wash Module 60V | Remove contamination from needle 54 with liquid cleansing solutions. |
| Wash Manifold | Connect needle 54 to Pump Module 60P |

TABLE 1-continued

| Module | Primary Functions |
| --- | --- |
| 60M Pump Module 60P | Pump reagent liquids and sample fluids. |
| Needle 54 | Aspirate and dispense reagent liquids and sample fluids. |

Figure 8:
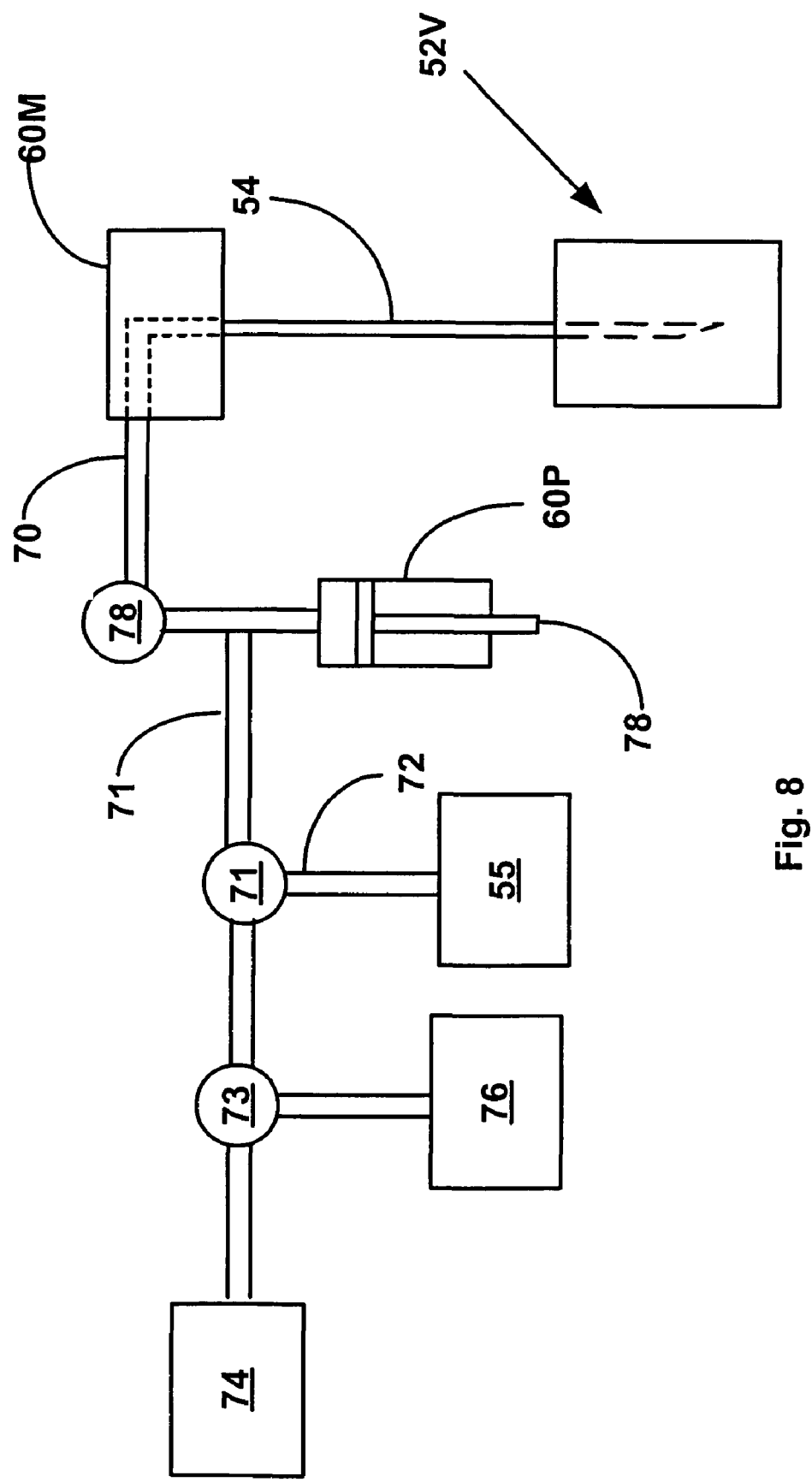
FIG. 8 is a schematic view of the liquid aspiration and dispensing system of FIG. 7 aspirating sample liquid from the aliquot vessel array of FIG. 3; and, FIG. 9 is a schematic view of the liquid aspiration and dispensing system of FIG. 8 dispensing sample liquid into the reaction cuvette of FIG. 2A.

FIG. 8 shows Pump Module 60P as comprising a piston-type Metering Pump 60P connected to liquid-carrying probe 54 supported by Manifold 60M, Manifold 60M being connected by a tube 70 to a conventional pressure measuring transducer 78 installed between Metering Pump 60P and Manifold 60M. Probe needle 54 preferably has a flat point designed to aid in eliminating variabilities that may exist at the lower end portion 54L of an aspirated liquid slug 54S and may be connected to Wash Manifold 60M using any of several screw-like connectors, not shown, or alternately, permanently welded thereto. Tube 71 connects Metering Pump 60P to: (1) a drain valve 72 connected to drain 55; and, from drain valve 72 to (2) a flush valve 73 connected to a flush pump 74 and a source of pressurized water 76. Metering Pump 60P is carefully controlled by computer 15 to precisely aspirate and dispense sample liquid like seen in FIGS. 6B and 6C. Pumping mechanisms other than a piston-type Metering Pump 60P may be employed to advantage in practicing the present invention as long as the pumping mechanism may be accurately controlled within the range of desired sample volumes.

FIG. 8 also illustrates probe needle 60N having entered an aliquot vessel 52V and positioned within a sample liquid contained therein. Level sensing means, for example using well known capacitive signals, may be advantageously employed in order to ensure that probe needle 60N is in fluid communication with the sample liquid. Metering Pump 60P is activated and the distance the piston 78 is moved is controlled by computer 15 so that a controlled volume of sample liquid is withdrawn or aspirated into probe needle 60N thereby forming slug 54S. The mechanisms for accurately controlling Metering Pump 60P so that an aspirated volume is in the range of about 1 microliter to five microliters include piston syringes driven by stepper motors (like those made by Cavro Co.) or a piston displacement in a sealed cavity where the piston is coupled to a stepper motor (like those made by Lee Co.). During this process, valve 71 is closed.

Figure 5:
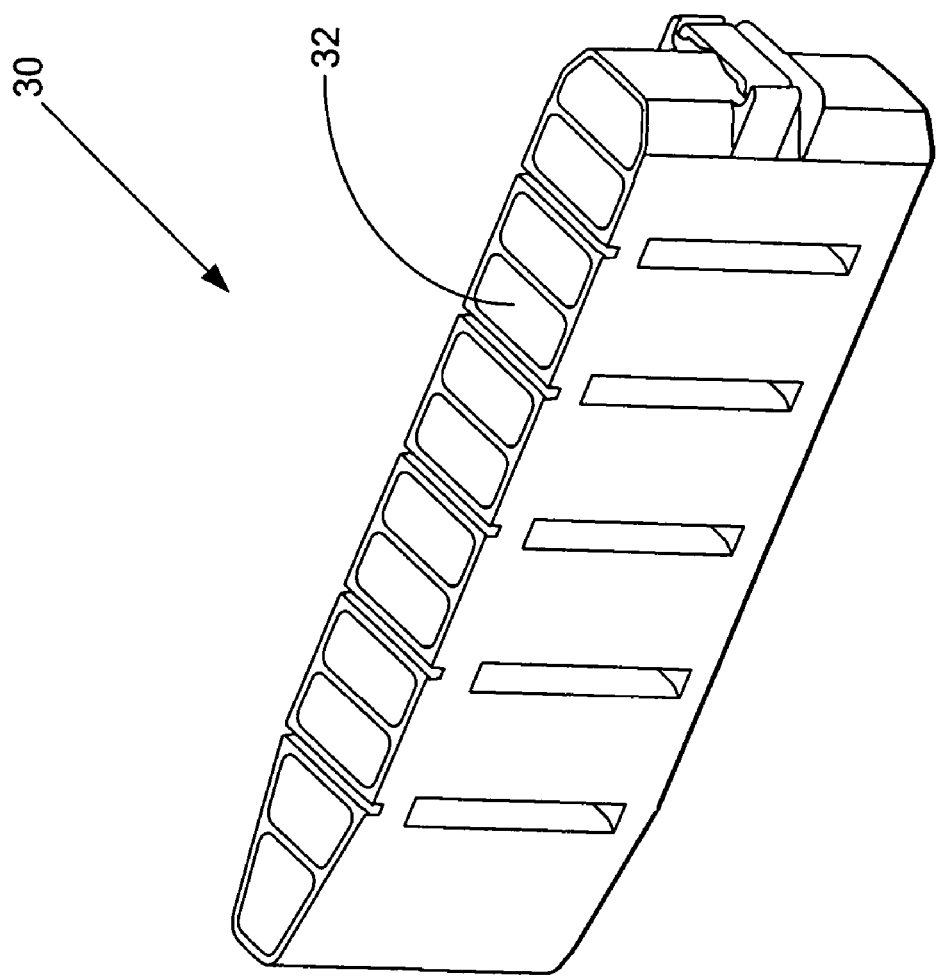
FIG. 5 is perspective view of a reagent cartridge useful in operating the analyzer of FIG. 1.
Figure 9:
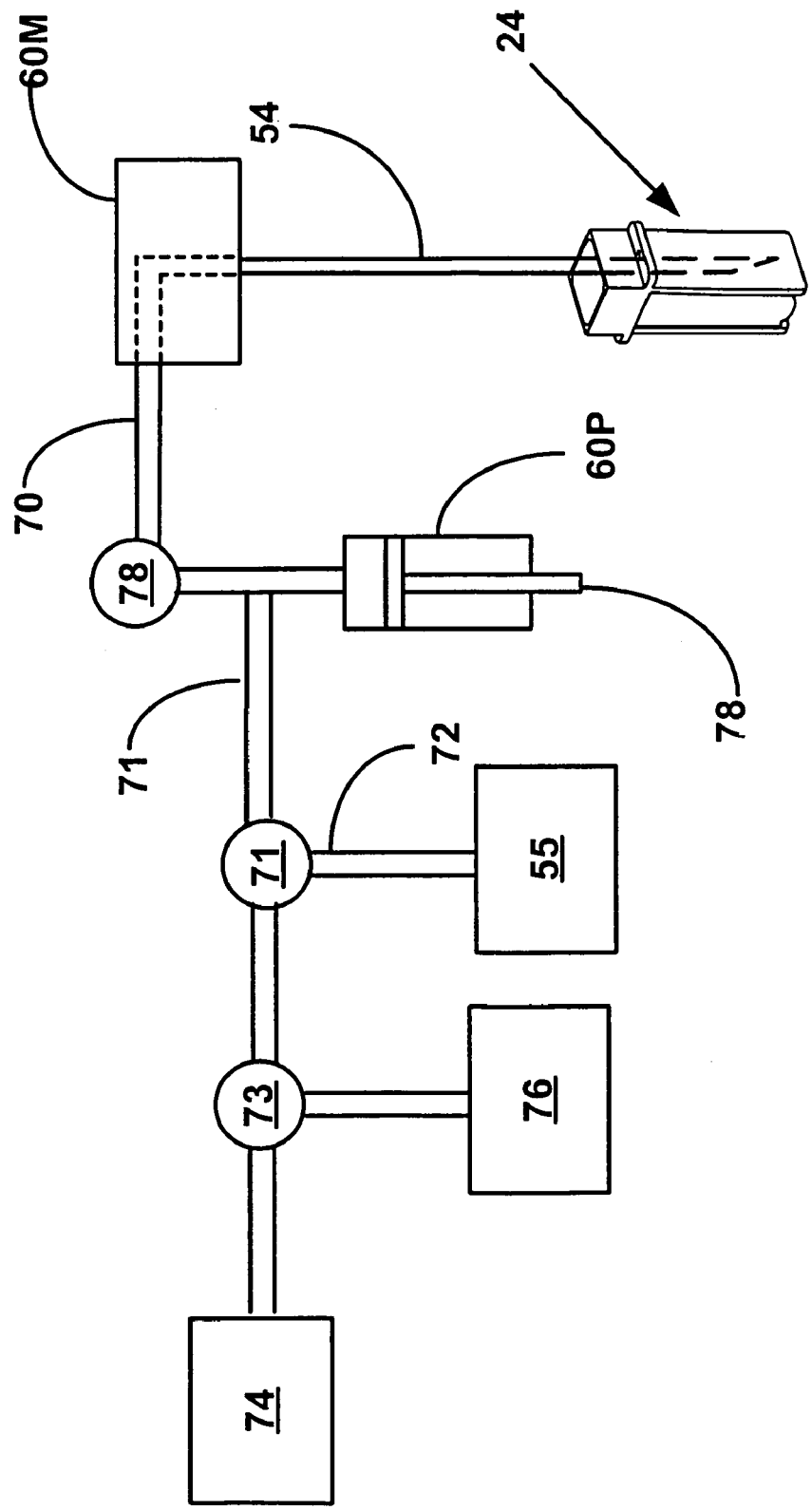

Temperature-controlled storage areas or servers 26, 27 and 28 inventory a plurality of multi-compartment elongate reagent cartridges 30, like that illustrated in FIG. 5 and described in co-pending application Ser. No. 09/949,132 assigned to the assignee of the present invention, containing reagents in wells 32 as necessary to perform a number of different assays. As described later in conjunction with FIG. 9, server 26 comprises a first carousel 26A in which reagent cartridges 30 may be inventoried until translated to a second carousel 26B for access by a reagent aspiration needle probe 60. FIG. 9 shows an advantageous embodiment in which carousel 26A and carousel 26B are circular and concentric, the first carousel 26A being inwards of the second carousel 26B. Reagent containers 30 may be loaded by placing such containers 30 into a loading tray 29 adapted to automatically translate containers 30 to a shuttling position described later.

Reagent aspiration needle probes 61 and 62 are independently mounted and translatable between servers 27 and 28, respectively and outer cuvette carousel 14. Probes 61 and 62 comprise conventional mechanisms for aspirating reagents required to conduct specified assays at a reagenting location from wells 32 in appropriate reagent cartridges 30, the probes 61 and 62 subsequently being shuttled to a dispensing location where reagents are dispensed into cuvettes 24.

During operation of analyzer 10 in conducting a typical clinical chemical assays, reagent aspiration needle probes 61 and 62 will be used to aspirate and dispense controlled amounts of reagent into a reaction cuvette 24 prior to sample being added therein. In such an instance, and contemplated by the present invention, the Pump Module 60P is operated to dispense the controlled amount of sample liquid from probe 54 when positioned near the bottom of the liquid receiving cuvette 24 as seen in FIG. 9. Probe 54 is then raised towards the top of the liquid mixture therein. While the sampling probe 54 is still within the sample-reagent mixture, a small amount of sample-reagent mixture illustrated by darkened rectangle 54M is aspirated into probe 54 as seen in FIG. 6D so that the sample liquid is safely trapped within probe 54. Probe 54 may then safely be used as a swizzle to mix the sample-reagent mixture without concern for unwanted sample to be dripped into cuvette 24 as would be likely if probe 54 was used as a mixing swizzle with sample at the lower end 54L of probe 54. Alternately, probe 54 may be raised above the top of the liquid mixture and a small amount of air illustrated by open rectangle 54A is aspirated into probe 54 as seen in FIG. 6E so that the sample liquid is safely trapped by an air bubble within probe 54. Any one of a number of mixing motions may be employed, an exemplary one of which is disclosed in co-pending application Ser. No. 11/032,356 assigned to the assignee of the present invention. It has been found that rapidly and repeatedly moving probe 54 in a two-dimensional parabolic or boomerang-curved pattern within the liquid mixture produces a surprisingly efficient mixing method. By rapidly and repeatedly moving probe 54 in a two-dimensional generally parabolic pattern within the solution. The probe 54 is attached to a moveable arm and the mixer reciprocates a moveable arm in a first direction and also reciprocates the arm in a second direction perpendicular to the first direction, so that probe 54 is moved in a generally parabolic pattern. In an exemplary embodiment, probe 54 is attached to a moveable arm having a protruding foot with a vertical roller pin in contact with a roller bearing. The moveable arm is vibrated by an alternating electromagnet in a first direction causing the roller pin to roll along the circumference of the roller bearing and the arm to move side-to-side in a in a second direction, generally perpendicular to the first direction. Varying the magnitude of movement of the moveable arm, in combination with adjusting the diameters of roller pin and roller bearing, produces a generally parabolic or generally boomerang-shaped ellipsoidal mixing pattern of probe 54 that has been found to be surprisingly efficient in time and effective in mixing uniformity. By using aspiration probe 54 as a mixing swizzle instead of the conventional practice of having a separate mixer, economy in production costs as well as space are achieved in addition to increasing overall system reliability by the elimination of a separate electromechanical device.

It should be readily appreciated by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A method for providing a desired volume of a first liquid within a biochemical analyzer, the method comprising the steps of:

aspirating a slug of the first liquid from a first container into a probe, the slug comprising an excess portion and a desired portion of the first liquid, ejecting a portion of the excess portion of the first liquid from the probe into a drain;

and then:

dispensing the desired volume of first liquid into a second container, wherein the second container has a second liquid therein: and wherein dispensing the desired volume of first liquid into a second container comprises:

positioning the probe near the bottom of the second container:

dispensing the desired volume of first liquid:

raising the probe towards the top of the second container still within the mixture of first and second liquids; and, aspirating a small volume of the mixture of first and second liquids into the probe.

2. The method of claim 1 wherein a portion of the first liquid remains in the probe after dispensing.

3. The method of claim 1 further comprising mixing the mixture of first and second liquids within the second container by lowering the probe into the second container and rapidly moving the probe in a mixing pattern.

4. The method of claim 1 wherein the first liquid is a liquid sample taken from a patient's infections, bodily fluids or abscesses and wherein the second liquid is a chemical reagent.

5. The method of claim 1 wherein the desired volume of the first liquid is in the range of 1-3 microliters.

6. The method of claim 3 wherein rapidly moving the probe in a mixing pattern comprises rapidly and repeatedly moving the probe in a generally parabolic or generally "boomerang-shaped" ellipsoidal mixing pattern within the liquid mixture.

* * * * *